US 7,858,811 B2

(12) United States Patent
Knipp et al.

(10) Patent No.: US 7,858,811 B2
(45) Date of Patent: Dec. 28, 2010

(54) PROCESS FOR THE PREPARATION OF INDOLES

(75) Inventors: Bernhard Knipp, Kuerten-Olpe (DE);
Ralf Kucznierz, Bad Duerkheim (DE);
Tim Sattelkau, Ludwigshafen (DE);
Thomas Zeibig, Mutterstadt (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/599,093

(22) Filed: Nov. 14, 2006

(65) Prior Publication Data

US 2007/0112054 A1 May 17, 2007

(30) Foreign Application Priority Data

Nov. 16, 2005 (EP) .................. 05110786

(51) Int. Cl.
*C07D 209/12* (2006.01)
(52) U.S. Cl. .................................... 548/493
(58) Field of Classification Search ........... 548/439, 548/493
See application file for complete search history.

(56) References Cited

U.S. PATENT DOCUMENTS

| 3,969,409 A | 7/1976 | Miyano et al. |
| 4,957,609 A | 9/1990 | Godfrey et al. |
| 2002/0061919 A1 | 5/2002 | Lee et al. |

FOREIGN PATENT DOCUMENTS

| DE | 23 23 301 | 11/1973 |
| EP | 0 353 983 A2 | 2/1990 |
| WO | 02/057199 | 7/2002 |
| WO | WO 03/006151 | 1/2003 |

OTHER PUBLICATIONS

Preliminary STN search results.*
Sakamoto et al, Synthesis, 1990, vol. 3, p. 215-218.*
Kasahara et al. Bull. Chem. Soc. Jpn., 1986, vol. 59, p. 927-928.*
Sorensen, Ulrik, S., et al., Helvetica Chimica Acta, 87(1), pp. 82-89 (2004), XP002420428.
Kudzma, Linas, V., Synthesis, (11), pp. 1661-1666 (2003), XP002420430.
Czeskis, Boris A., et al., Journal of Labelled Compounds & Radiopharmaceuticals, 48(6) pp. 407-419 (2005), XP002420431.
Sakamoto et al., Synthesis, pp. 215 (1990).
Iida et al., J. Org. Chem., 44, pp. 1236-1241 (1979).
Tan et al., Tetrahedron Letters, 39, pp. 4187-4190 (1998).
Jang, S.-B., Tetrahedron Letters, 38, pp. 4421-4424 (1997).
Miller et al., Org. Lett., 5, pp. 285-287 (2003).
Köhler et al., Chem. Eur. J., 8, pp. 622-631 (2002.
Wang et al., Journal of the Chinese Chemical Society, 42, pp. 593-595 (1995).
Arcadi, A., et al., Green Chemistry, 5(1), pp. 64-67, XP009082949 (2003), published online Nov. 28, 2002.
Zhang, Zhan-Hui, et al., Advanced Synthesis & Catalysis, 348(1+2), pp. 184-190 (2006), XP00243119.
Suzuki, Hitomi, et al., Synthesis, (7), pp. 616-617 (1984), XP002431140.

* cited by examiner

*Primary Examiner*—Yong Chu
(74) *Attorney, Agent, or Firm*—George W. Johnston; Dennis P. Tramaloni

(57) ABSTRACT

A process for the preparation of indoles, e.g. 1,2,3,9-tetrahydro-carbazol-4-one and derivatives thereof.

4 Claims, No Drawings

PROCESS FOR THE PREPARATION OF INDOLES

This application claims the benefit of European Application No. 05110786.0, filed Nov. 16, 2005, which is hereby incorporated by reference in its entirety.

The present invention relates to a process for the preparation of indoles, e.g. 1,2,3,9-tetra-hydro-carbazol-4-one and derivatives thereof.

1,2,3,9-tetrahydro-carbazol-4-one (THOC) and derivatives thereof can be used as intermediates in the process for the preparation of e.g. valuable active substances in medicaments, e.g. as an intermediate in the process for the preparation of a carbazolyl-(4)-oxypropanolamine derivative of formula

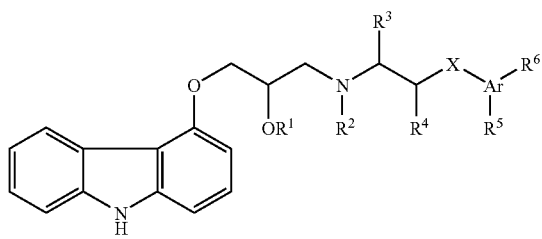

wherein

X is a bond, —$CH_2$—, an oxygen or sulfur atom;

Ar is phenyl, naphthyl, indanyl or tetrahydronaphthyl;

$R^1$ is hydrogen, $C_1$-$C_6$alkyl, benzyl or naphthyl;

$R^2$ is hydrogen, $C_1$-$C_6$alkyl or ar$C_1$-$C_6$alkyl selected from benzyl, phenylethyl and phenylpropyl;

$R^3$ is hydrogen or $C_1$-$C_6$alkyl;

$R^4$ is hydrogen or $C_1$-$C_6$alkyl, or when X is an oxygen atom, $R^4$ together with $R^5$ is —$CH_2O$—;

$R^5$ and $R^6$ are independently of each other hydrogen, halogen, hydroxy, $C_1$-$C_6$alkyl, —$CONH_2$—, $C_1$-$C_6$alkoxy, benzyloxy, $C_1$-$C_6$alkylthio, $C_1$-$C_6$alkylsulphinyl or $C_1$-$C_6$alkylsulphonyl; or $R^5$ and $R^6$ together represent methylenedioxy, e.g. of (1-(carbazol-4-yloxy-3-((2-(o-methoxyphenoxy)ethyl)amino)-2-propanol (e.g. EP 004,920) or carvedilol. A medicament containing carvedilol for the treatment of patients suffering from hypertension or congestive heart failure is commercially available, e.g. under the tradename of Dilatrend®.

In one embodiment the present invention provides a process for the preparation of a compound of formula I

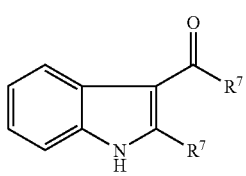

wherein both R7 are, independently, $C_1$-$C_6$alkyl, or together are —$CH_2$—$CH_2$—$CH_2$—;

comprising cyclizing a compound of formula II

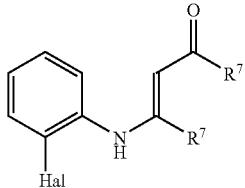

wherein both R7 are, independently, $C_1$-$C_6$alkyl, or together are —$CH_2$—$CH_2$—$CH_2$—; and Hal is halogen, e.g. I, Br or Cl;

in the presence of a palladium catalyst in an amount in the range from 0.00001 to lower than 5 mol %.

Examples of a palladium catalyst include Pd organic compounds, like Pd(PPh$_3$)$_4$ wherein Ph is phenyl, trans-di(μ-acetato)bis[o-(di-o-tolylphosphino)benzyl]dipalladium (II), and bis(acetonitrile)-palladium(II)chloride, palladium salts like PdCl$_2$ or another salt without addition of ligands, e.g. palladium acetate; and palladium catalysts on a solid support, like Pd(PPh$_3$)$_4$ polymer bound, e.g. commercially available from suppliers like Aldrich, e.g. catalog number 511579, and 5% Pd/C, e.g. 5% Pd/C 50% H$_2$O type E105 CA/W, or type E10N/W; 10% Pd/C, e.g. 10% Pd/C 50% H$_2$O type K-0220 from suppliers like Heraeus and Degussa; and a microencapsulated palladium catalyst.

Examples of a microencapsulated palladium catalyst include catalysts prepared by immobilizing palladium, e.g. colloidal palladium or palladium acetate, optionally with activating ligands, within a permeable polymer microcapsule shell. For example, a microencapsulated catalyst may be prepared by dissolving or dispersing a catalyst in a first phase (e.g. an organic phase), dispersing the first phase in a second, continuous phase (e.g. an aqueous phase) to form an emulsion, reacting one or more microcapsule wall-forming materials at the interface between the dispersed first phase and the continuous second phase to form a microcapsule polymer shell encapsulating the dispersed first phase core and optionally recovering the microcapsules from the continuous phase. The encapsulated catalyst may be recovered from the reaction medium and recycled as is described e.g. in WO2003006151, e.g. within a highly cross-linked polyurea matrix, e.g. Pd(0) EnCat™ NP (30% Matrix content, 0.4 mmol Pd/g) which is commercially available from Sigma-Aldrich, e.g. under catalog number 65,366-7.

The reaction may take place in a solvent like NMP, DMF, ethanol or H$_2$O in ethanol.

The reaction may take place in the presence of a base like NaOH and organic bases like triethylamine and tripropylamine or of a salt of an organic or inorganic acid like sodium acetate, NaHCO$_3$ or Na$_2$CO$_3$.

The process may be performed at a temperature in the range from room temperature (RT) to the corresponding boiling point of the solvent used, e.g. at 135° C. or 140° C.

The process may be performed during a time period of from 1 hour to 72 hours, e.g. for 20 hours or 14 hours, e.g. overnight.

The process may be performed in the presence of an additional extra ligand, e.g. tetra-phenylphosphonium chloride.

The catalyst may be removed from the reaction mixture by procedures known to the skilled artisan, e.g. by extraction or by suction. The removal may take place at a temperature in the range from RT to below the corresponding boiling point, e.g. in a range from 80 to 90° C. The removed catalyst may be washed once or several times with a solvent, e.g. with the solvent used in the reaction, e.g. with NMP.

By the above process the compound of formula I may be obtained in a yield of from 35 to 100%, e.g. 60 to 90%, e.g. 70 to 90%, e.g. 80 to 90%. For example, the compound of formula I may be obtained from a compound of formula II wherein Hal is Br or I, in a yield from 70 to 100%, e.g. from 80 to 90%; or the compound of formula I may be obtained from a compound of formula II wherein Hal is Cl, in a yield from 35 to 100%, e.g. from 35 to 70%.

By the above process the compound of formula I may be obtained with a purity from 50 to 99.5% (HPLC), e.g. 90 to 99.5% (HPLC), e.g. 98 to 99.5% (HPLC).

By purification by e.g. stirring or decoction or crystallization in an organic solvent, in a mixture of an organic solvent and water or in water, e.g. ethanol or ethanol/water or water the compound of formula I prepared by the above process may be obtained in a purity of 98 to 100% (HPLC), e.g. 99.5 to 100% (HPLC).

In another embodiment the present invention provides a process for the preparation of a compound of formula I comprising cyclizing a compound of formula II in the presence of a palladium catalyst in an amount in the range from 0.00001 to lower than 5 mol % wherein in formulae I and II both $R^7$ together are —$CH_2$—$CH_2$—$CH_2$—.

In another embodiment the present invention provides a process for the preparation of a compound of formula I comprising cyclizing a compound of formula II in the presence of a palladium catalyst in an amount in the range from 0.00001 to 1 mol %, e.g. in the range from 0.001 to 0.9 mol %, e.g. in the range from 0.01 to 0.5 mol %, e.g. from 0.1 to 0.2 mol %. In another embodiment the present invention provides a process for the preparation of a compound of formula I comprising cyclizing a compound of formula II wherein Hal is Cl in the presence of a palladium catalyst. In still another embodiment the present invention provides a process for the preparation of a compound of formula I comprising cyclizing a compound of formula II wherein Hal is Cl in the presence of bis(acetonitrile)-palladium(II)chloride.

In another embodiment the present invention provides a process for the preparation of a compound of formula I comprising cyclizing a compound of formula II wherein Hal is I or Br in the presence of a palladium catalyst in $C_1$-$C_4$alkanol; a palladium salt; or a palladium catalyst on a solid support.

Examples of a palladium catalyst in $C_1$-$C_4$alkanol include $Pd(PPh_3)_4$ wherein Ph is phenyl in $C_1$-$C_4$alkanol and trans-di (o-acetato)bis[o-(di-o-tolylphosphino)benzyl]dipalladium (II) in $C_1$-$C_4$alkanol. Examples of $C_1$-$C_4$alkanol include methanol, ethanol, propanol and its isomers, and butanol and its isomers.

In another embodiment the present invention provides a composition containing a compound of formula I and traces of Pd or palladium salt, e.g. 0.001-1 µg Pd/mg THOC (I).

The compound of formula II may be prepared by a procedure known to the skilled artisan or by the following procedure.

In another embodiment the present invention provides a process for the preparation of a compound of formula II wherein both R7 are, independently, $C_1$-$C_6$alkyl, or together are —$CH_2$—$CH_2$—$CH_2$— comprising reacting a compound of formula III

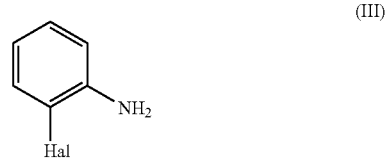

(III)

wherein Hal is halogen, e.g. Cl, Br or I;

with a compound of formula IV

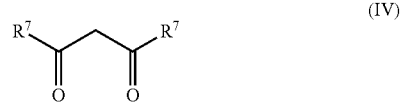

(IV)

wherein both R7 are, independently, $C_1$-$C_6$alkyl, or together are —$CH_2$—$CH_2$—$CH_2$—;

followed by crystallization.

In still another embodiment the present invention provides a process for the preparation of a compound of formula II wherein both $R^7$ together are —$CH_2$—$CH_2$—$CH_2$— comprising reacting a compound of formula III

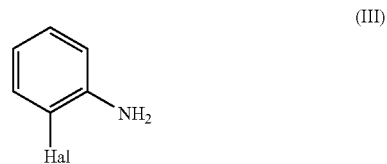

(III)

wherein Hal is halogen, e.g. Cl, Br or I;

with a compound of formula IV

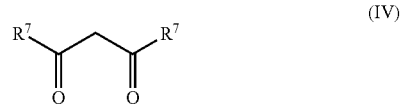

(IV)

wherein both $R^7$ together are —$CH_2$—$CH_2$—$CH_2$—;

followed by crystallization.

The reaction may take place in the presence of an acid, e.g. an organic acid, e.g. acetic acid or propionic acid, or homologs thereof. The ratio of the acid in the reaction mixture may be between 0 and 50 weight %, e.g. between 15 and 25 weight %. The reaction may take place at a temperature in the range from RT to a temperature below the boiling point, e.g. at 60° C. The reaction may take place in a nitrogen atmosphere.

The crystallization of the compound of formula II may be initiated by the addition of water. By the above process the compound of formula II may be obtained in a yield of from 85% to quantitative yield, e.g. 98%.

The compounds of formula III and IV are commercially available or may be prepared by procedures known to the skilled artisan.

In another embodiment the present invention provides a process for the preparation of a compound of formula I

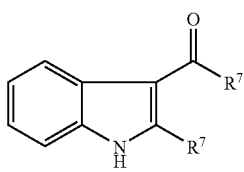
(I)

wherein both R7 are, independently, $C_1$-$C_6$alkyl, or together are —$CH_2$—$CH_2$—$CH_2$—;

wherein (a) a compound of formula III

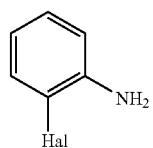
(III)

wherein Hal is halogen, e.g. Cl, Br or I;

is reacted with a compound of formula IV

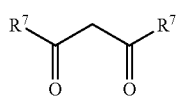
(IV)

wherein both R7 are, independently, $C_1$-$C_6$alkyl, or together are —$CH_2$—$CH_2$—$CH_2$—;

in the presence of an acid or a mixture of an acid and an organic solvent;

(b) followed by optional addition of extra solvent, and by neutralization with a base, and (c) cyclization in the presence of a metal catalyst and a base.

The above process is referred to hereinafter as the ONE POT REACTION. In another embodiment the present invention provides a ONE POT REACTION for the preparation of a compound of formula I wherein in formulae I and IV both $R^7$ together are —$CH_2$—$CH_2$—$CH_2$—.

Examples of a metal catalyst include a transition metal catalyst, e.g. a palladium catalyst, a rhodium catalyst and a ruthenium catalyst, e.g. a palladium catalyst like the ones mentioned above.

Examples of an acid include an organic acid, e.g. acetic acid or propionic acid, or homologs thereof.

Examples of a base include NaOH, mineral alkaline agents like $NaHCO_3$ and $Na_2CO_3$, salts of organic acids like sodium acetate, and organic bases like triethylamine and tripropylamine.

Neutralization may take place by neutralization of an acid with a mineral alkaline agent or an organic base, e.g. by neutralization of an organic acid like acetic acid with a mineral alkaline agent like sodium hydroxide, an aqueous solution thereof, or with an organic base like triethylamine or tripropylamine. After neutralization, water may be eliminated by a process known to the skilled person, e.g. by distillation.

After the neutralization step an additional base may be added to the mixture.

The ONE POT REACTION may be performed by addition of a solvent like NMP, DMF, ethanol or $H_2O$ in ethanol to the reaction mixture. The solvent may be added at different stages of the process, e.g. before or after the neutralization.

The amount of the solvent may be in the range from 20 to 90 weight %, e.g. from 50 to 70 weight %.

The temperature at which the ONE POT REACTION may be performed is depending on whether the catalyst had already been added or not. For example, prior to the addition of the catalyst the temperature may be in the range from RT to 100° C., e.g. 60° C. Following the addition of catalyst the temperature may be raised up to the corresponding boiling point of the solvent used, e.g. at 135° C. or 140° C.

The catalyst may be removed from the reaction mixture by procedures known to the skilled artisan, e.g. by extraction or by suction. The removal may take place at a temperature in the range from RT to below the corresponding boiling point, e.g. in a range from 80 to 90° C. The removed catalyst may be washed once or several times with a solvent, e.g. with the solvent used in the reaction, e.g. with NMP.

By the ONE POT REACTION the compound of formula I may be obtained in a yield of from 35 to 100%, e.g. 60 to 90%, e.g. 70 to 90%, e.g. 80 to 90%. For example, if in the ONE POT REACTION a compound of formula III, wherein Hal is Br or I, is used the compound of formula I may be obtained in a yield from 70 to 100%, e.g. from 80 to 90%; or if a compound of formula III, wherein Hal is Cl, is used the compound of formula I may be obtained in a yield from 35 to 100%, e.g. from 35 to 70%

By the ONE POT REACTION the compound of formula I may be obtained in a purity from 50 to 99.5% (HPLC), e.g. from 90 to 99.5% (HPLC), e.g. 97 to 99.5% (HPLC).

By purification by e.g. stirring or decoction or crystallization in an organic solvent, in a mixture of an organic solvent and water or in water, e.g. ethanol or ethanol/water or water the compound of formula I prepared by the ONE POT REACTION may be obtained in a purity of 98 to 100% (HPLC), e.g. 99 to 100% (HPLC).

The catalyst may be added to the reaction mixture after the neutralization.

EXAMPLES

The following abbreviations were used throughout the specification: RT: room temperature; DMF: N,N-dimethylformamide; NMP: N-methyl-2-pyrrolidone.

Preparation of a Compound of Formula II

Example 1.1

Preparation of 3-(2-bromoanilino)-cyclohex-2-enone
(II, Hal=Br, Both $R^7$ Together are —$CH_2$—$CH_2$—$CH_2$—)

22.3 g (130 mmol) of 2-bromoaniline (III, Hal=Br) and 15.0 g (134 mmol) of 1,3-cyclo-hexanedione (IV, both $R^7$ together are —$CH_2$—$CH_2$—$CH_2$—) were dissolved in 18.5 ml of acetic acid at 25° C. under nitrogen. The mixture was stirred for 3 hours at 25° C. A homogenous suspension was formed. 74 ml of water were added within 30 min at 25° C., the suspension was stirred for additional 90 min. The solid was filtered off, washed with 60 ml of water and dried at 50° C. for 12 hours. Yield: 33.9 g (98%), m.p. 164-170° C.

Example 1.2

Preparation of 3-(2-chloroanilino)-cyclohex-2-enone (II, Hal=Cl, Both $R^7$ Together are —$CH_2$—$CH_2$—$CH_2$—)

16.5 g (129 mmol) of 2-chloroaniline (III, Hal=Cl) and 15.0 g (134 mmol) of 1,3-cyclo-hexanedione (IV, both $R^7$ together are —$CH_2$—$CH_2$—$CH_2$—) were dissolved in 18.5 ml of acetic acid at 25° C. under nitrogen. The mixture was stirred for 3 hours at 25° C. A clear, yellow-brownish solution was formed. 74 ml of water were added within 30 min at 25° C., the suspension was stirred for additional 90 min. The solid was filtered off, washed with 60 ml of water and dried at 50° C. for 12 hours. Yield: 27.5 g (96%), m.p. 171-172° C.

Preparation of a Compound of Formula I Starting from a Compound of Formula II

Example 2.1

Preparation of THOC (I, Both $R^7$ Together are —$CH_2$—$CH_2$—$CH_2$—)

(a) 2.66 g (10 mmol) of 3-(2-bromoanilino)-cyclohex-2-enone (II, Hal=Br, both $R^7$ together are —$CH_2$—$CH_2$—$CH_2$—), 240 mg (0.2 mmol) of Pd(PPh$_3$)$_4$, 50 ml of EtOH and 2 ml of triethylamine were heated under stirring and nitrogen atmosphere to 80° C. After 28 h 1 ml of triethylamine was added and heating continued for further 20 h. The mixture was concentrated to 25 ml and cooled to 0° C. The precipitation was separated, washed with 5 ml of EtOH (0° C.), dried (50° C.), stirred (1 h) with 25 ml of water (RT), isolated and dried (50° C.). Yield: 82% THOC (I), m.p. identical with an authentic sample. Purity: 99.8% (HPLC)

(b) 2.66 g (10 mmol) of 3-(2-bromoanilino)-cyclohex-2-enone (II, Hal=Br, both $R^7$ together are —$CH_2$—$CH_2$—$CH_2$—), 250 mg (0.2 mmol) of Pd(PPh$_3$)$_4$ polymer bound (0.79 mmol Pd/g), 35 ml of EtOH, 1 ml of water and 3 g (30 mmol) of Na$_2$CO$_3$ were heated under stirring and nitrogen atmosphere to 80° C. After 44 h 125 mg (0.1 mmol) of Pd(PPh$_3$)$_4$ polymer bound (0.79 mmol Pd/g) was added and heating continued for further 22 h. The warm mixture was filtrated and the residue was washed with 5 ml of EtOH (75° C.). The filtrate was cooled to 0° C. The precipitation was separated, washed with 5 ml of EtOH (0° C.), dried (50° C.), stirred (1 h) with 25 ml water (RT), isolated and dried (50° C.). Yield: 70% THOC (I), m.p. identical with an authentic sample. Purity: 99.9% (HPLC).

(c) 8 g (30 mmol) of 3-(2-bromoanilino)-cyclohex-2-enone (II, Hal=Br, both $R^7$ together are —$CH_2$—$CH_2$—$CH_2$—), 10 mg (0.0446 mmol) of Pd(OAc)$_2$, 12 ml of NMP and 2.95 g (36 mmol) of NaOAc were heated under stirring and nitrogen atmosphere to 135° C. for 41 h. The warm mixture (85° C.) was filtrated and the residue was washed with 5 ml of NMP. The filtrate was added to 30 ml of HCl (2 m)/90 ml of water. The precipitation was separated, washed with 60 ml of water, dried (50° C.), crude yield: 79% THOC (I), m.p. 210-212° C.; recrystallized with charcoal from 60 ml of 95% EtOH and dried (50° C.). Yield: 70% THOC (I), m.p. identical with an authentic sample. Purity: 99.4% (HPLC).

(d) 32 g (120 mmol) of 3-(2-bromoanilino)-cyclohex-2-enone (II, Hal=Br, both $R^7$ together are —$CH_2$—$CH_2$—), 1.6 g (0.376 mmol) of 5% Pd/C 50% H$_2$O type E105 CA/W, 48 ml of NMP and 11.8 g (144 mmol) of NaOAc were heated under stirring and nitrogen atmosphere to 135° C. for 20 h. The warm mixture (85° C.) was filtrated and the residue was washed with 8 ml of NMP. The filtrate was added to 120 ml of HCl (2 m)/360 ml of water. The precipitation was separated, washed with 200 ml of water, dried (50° C.); crude yield: 83% THOC (I), m.p. 214-216° C., purity: 98.0% (HPLC); recrystallized with charcoal from 240 ml of 95% EtOH and dried (50° C.). Yield: 61% THOC (I), m.p. identical with an authentic sample. Purity: 99.7% (HPLC).

(e) 32 g (120 mmol) of 3-(2-bromoanilino)-cyclohex-2-enone (II, Hal=Br, both $R^7$ together are —$CH_2$—$CH_2$—$CH_2$—), 0.188 mmol of Pd catalyst (table 1), 50 ml of NMP and 11.8 g (144 mmol) of NaOAc were heated under stirring and nitrogen atmosphere to 135° C. for the required reaction time (table 1). The warm mixture (85° C.) was filtrated and the residue was washed with NMP. The filtrate was concentrated under reduced pressure to 25 ml and the suspension added to 30 ml of HCl (2 m)/90 ml of water. The precipitation was separated, washed with 200 ml of water, dried (50° C.); crude yield (m.p.) THOC (I) in table 1; recrystallized with charcoal from 95% EtOH and dried (50° C.). Yield [%] (table 1), m.p. of recrystallized THOC (I) identical with an authentic sample, purity [%] (table 1).

TABLE 1

| Pd catalyst | reaction time [h] | crude yield [%] THOC (I) (m.p. [° C.]) | yield [%] THOC (I) | purity [%] (HPLC) |
| --- | --- | --- | --- | --- |
| 800 mg 5% Pd/C 50% H$_2$O type E105 CA/W | 20 | 88 (206-208) | 63 | 99.7 |
| 800 mg 5% Pd/C 50% H$_2$O type E10N/W | 20 | 90 (202-209) | 66 | 99.7 |
| 400 mg 10% Pd/C 50% H$_2$O type K-0220 | 72 | 77 (194-202) | 50 | 99.7 |

(f) To 100 mg (0.39 mmol) of bis(acetonitrile)-palladium (II)chloride and 1.5 g (4 mmol) of tetraphenylphosphonium chloride were added 3.7 g (45 mmol) of NaOAc and 5.0 g (23 mmol) of 3-(2-chloroanilino)-cyclohex-2-enone (II, Hal=Cl, both $R^7$ together are —$CH_2$—$CH_2$—$CH_2$—) under an argon atmosphere. After addition of 22.5 ml of DMF the mixture was stirred 20 hours at 150° C. After cooling to 20° C. the solid was filtered off and washed with DMF. The filtrate was added to 280 ml water and after stirring for 30 min the mixture was extracted twice with 150 ml of ethyl acetate. After filtration over activated charcoal the ethyl acetate solution was concentrated to dryness. The residue was stirred with methyl-t-butylether. After filtration and drying the raw material (crude yield: 60% THOC (I), purity: 90.7% (HPLC) was recrystallized from EtOH. Yield: 36% THOC (I), m.p. identical with an authentic sample. Purity: 99.0% (HPLC).

Preparation of a Compound of Formula I in a One-Pot Reaction

Example 3.1

Preparation of THOC (I, Both $R^7$ Together are —$CH_2$—$CH_2$—$CH_2$—)

22.6 g (131 mmol) of 2-bromoaniline (III, Hal=Br) and 15.2 g (136 mmol) of 1,3-cyclo-hexanedione (IV, both $R^7$ together are —$CH_2$—$CH_2$—$CH_2$—) were dissolved in 13.5 ml of acetic acid at 60° C. under nitrogen. The mixture was stirred 3 hours at 60° C., then 74.5 ml of NMP were added within 30 min. Subsequently, 17 g of sodium hydroxide solution (50%) were added at a temperature below 70° C. within 30 min. Pd catalyst (table 2) was added to the mixture. Water/NMP was distilled off till a pot temperature of 140° C. Heating at 135° C. was continued under stirring for 20 h. The warm mixture (85° C.) was filtered and the residue was washed with NMP. The filtrate was concentrated under reduced pressure to 25 ml and 30 ml of HCl (2 m)/90 ml of water were added. The precipitation was separated, washed with 200 ml of water, dried (50° C.); crude yield THOC (I) and purity (HPLC) in table 2; decocted with EtOH or recrystallized with charcoal from 95% EtOH and dried (50° C.). Yield [%] (table 2), m.p. identical with an authentic sample, purity [%] (table 2).

TABLE 2

| Pd catalyst | yield [%] THOC (I) crude/decoct./recryst. | purity [%] (HPLC) crude/decoct./recryst. |
|---|---|---|
| 870 mg (0.205 mmol) 5% Pd/C 50% H$_2$O type E105 CA/W | 86/78/68 | 98.4/99.7/99.8 |
| 870 mg (0.205 mmol) 5% Pd/C 50% H$_2$O type E10 N/W | 85/75/66 | 98.3/99.7/99.8 |
| 400 mg (0.16 mmol) Pd(0)EnCat ™ NP (30% Matrix content, 0.4 mmol Pd/g) | 82/71/63 | 98.0/99.0/99.1 |

Example 3.2

Preparation of THOC (I, Both R$^7$ Together are —CH$_2$—CH$_2$—CH$_2$—)

2.9 g (13.1 mmol) of 2-iodoaniline (III, Hal=I) and 1.52 g (13.6 mmol) of 1,3-cyclohexanedione (IV, both R$^7$ together are —CH$_2$—CH$_2$—CH$_2$—) were dissolved in 1.4 ml of acetic acid at 60° C. under nitrogen. The mixture was stirred for 3 hours at 60° C., then 7.5 ml of NMP were added within 30 min. Subsequently, 1.7 g of sodium hydroxide solution (50%) were added at a temperature below 70° C. within 30 min. 87 mg (0.0205 mmol) of 5% Pd/C 50% H$_2$O type E105 CA/W was added to the mixture. Water/NMP was distilled off till a temperature of 140° C. was reached. Heating at 135° C. was continued under stirring for 20 h. The warm mixture (85° C.) was filtrated and the residue was washed with NMP. The filtrate was concentrated under reduced pressure to 2.5 ml and 9 ml of water were added. The precipitation was separated, washed with 20 ml of water, dried (50° C.), decocted with EtOH and dried (80° C., vacuum drying oven). Yield: 33% THOC (I), m.p. identical with an authentic sample. Purity: 98.8% (HPLC). Additional THOC (I) can be isolated via silica gel column chromatography. Yield: 13% THOC (I), m.p. 209-212° C., purity: 89.9% (HPLC).

Example 3.3

Preparation of THOC (I, Both R$^7$ Together are —CH$_2$—CH$_2$—CH$_2$—)

45.2 g (263 mmol) of 2-bromoaniline (III, Hal=Br) and 30.4 g (271 mmol) of 1,3-cyclo-hexanedione (IV, both R$^7$ together are —CH$_2$—CH$_2$—CH$_2$—) were dissolved in 18 ml of acetic acid and 14 ml of NMP at 60° C. under nitrogen. The mixture was stirred for 3 hours at 60° C., then 135 ml of NMP were added within 30 min. Subsequently, 25 g of sodium hydroxide solution (50%) were added at a temperature below 70° C. within 30 min. 1.8 g (0.423 mmol) of 5% Pd/C 50% H$_2$O type E105 CA/W was added to the mixture. Water/NMP was distilled off till a temperature of 140° C. was reached. Heating at 140° C. was continued under stirring for 20 h. The warm mixture (90° C.) was filtered and the residue was washed with NMP. The filtrate was concentrated under reduced pressure to 50 ml and 60 ml of HCl (2 m)/180 ml of water were added. The precipitation was separated, washed with 400 ml of water, dried (50° C.); crude yield: 86% THOC (I), purity 97.1% (HPLC); decocted with ethanol/water (95/5) and dried (50° C.). Yield 78% THOC (I), m.p. identical with an authentic sample. Purity: 99.5% (HPLC).

The compound of formula I may e.g. be used as a starting compound in a synthesis according to the following scheme:

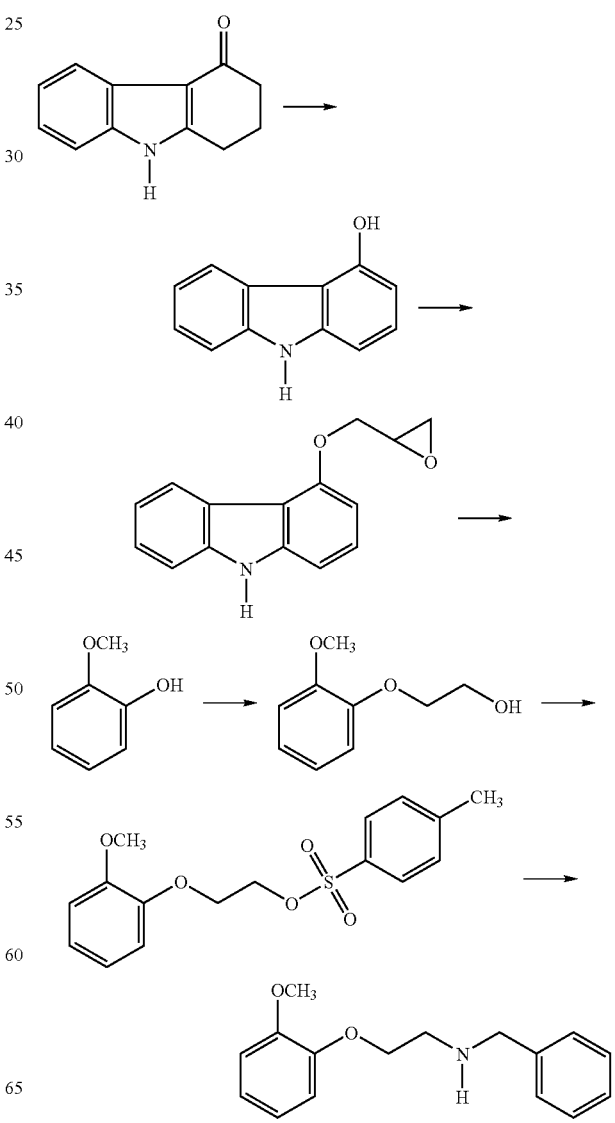

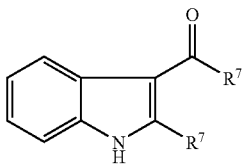

The invention claimed is:
1. A process for the preparation of a compound of formula I

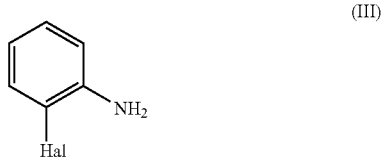

wherein both $R^7$ are, independently, $C_1$-$C_6$alkyl, or together are —$CH_2$—$CH_2$—$CH_2$—; wherein
(a) a compound of formula III (III)

wherein Hal is halogen;
is reacted with a compound of formula IV (IV)

wherein both $R^7$ are, independently, $C_1$-$C_6$alkyl, or together are —$CH_2$—$CH_2$—$CH_2$—;
in the presence of an acid, or a mixture of an acid and an organic solvent, and tetraphenyl phosphonium chloride;
(b) followed by optional addition of extra solvent, and by neutralization with a base, and
(c) cyclization in the presence of a palladium catalyst and a base.

2. The process according to claim 1 wherein in formulae I and IV both $R^7$ together are —$CH_2$—$CH_2$—$CH_2$—.

3. The process according to claim 1 wherein the palladium catalyst is Pd(PPh$_3$)$_4$, wherein Ph is phenyl, trans-di(μ-acetato)bis[o-(di-o-tolylphosphino)benzyl]dipalladium (II), bis(acetonitrile)-palladium(II)chloride, a palladium salt or a palladium catalyst on a solid support.

4. The process according to claim 1 wherein the palladium catalyst is added to the reaction mixture after neutralization.

* * * * *